United States Patent [19]

Yafuso et al.

[11] Patent Number: 4,824,789
[45] Date of Patent: Apr. 25, 1989

[54] GAS SENSOR

[75] Inventors: Masao Yafuso, El Toro; John K. Suzuki, San Juan Capistrano, both of Calif.

[73] Assignee: Cardiovascular Devices, Inc., Irvine, Calif.

[21] Appl. No.: 917,912

[22] Filed: Oct. 10, 1986

[51] Int. Cl.[4] .................... G01N 33/49; G02B 6/02
[52] U.S. Cl. ............................ 436/68; 128/634; 250/227; 356/39; 422/58; 422/83; 436/133; 436/172
[58] Field of Search .............. 422/58, 83; 436/133, 436/68, 172; 128/634; 356/39; 250/227

[56] References Cited

U.S. PATENT DOCUMENTS

| | | | |
|---|---|---|---|
| Re 31,879 | 5/1985 | Lübbers et al. | 436/133 |
| 3,335,715 | 8/1967 | Hugenholtz et al. | 128/634 |
| 3,674,013 | 7/1972 | Polanyi | 128/634 |
| 3,822,695 | 7/1974 | Takayama | 128/634 |
| 3,866,599 | 2/1975 | Johnson | 128/634 |
| 3,904,373 | 9/1975 | Harper | 435/169 X |
| 4,194,877 | 3/1980 | Peterson | 128/634 X |
| 4,200,110 | 4/1980 | Peterson et al. | 422/58 X |
| 4,487,206 | 12/1984 | Aagard | 128/634 X |
| 4,509,522 | 4/1985 | Manuccia et al. | 128/634 |
| 4,560,248 | 12/1985 | Cramp et al. | 128/634 X |
| 4,577,109 | 3/1986 | Hirschfeld | 250/461.1 |

OTHER PUBLICATIONS

Zhujun et al., Analytica Chimica Acta 160, (1984), pp. 305–309.

Primary Examiner—Barry S. Richman
Assistant Examiner—Jill Johnston
Attorney, Agent, or Firm—Frank J. Uxa, Jr.; Gordon L. Peterson

[57] ABSTRACT

A gas sensor has a first aqueous phase. The aqueous phase is composed of a soluble dye in a buffer. One or more additional agent can be further added to the aqueous phase as for instance an emulisification enhancement agent. The aqueous phase is homogenized into a polymeric precursor forming a emulsion of the aqueous phase in the polymeric precursor. A catalyst and a cross-linking agent are added and the polymeric precursor material allowed to polymerize to form an emulsoid of micro-compartments of the aqueous phase in a polymeric second phase. The micro-compartments of the aqueous phase are dispersed through and permanently suspended in the polymeric second phase.

26 Claims, 1 Drawing Sheet

$\lambda ex$  $\lambda em$

GAS SENSOR

BACKGROUND OF THE INVENTION

This invention is directed to an improved gas sensor for sue in sensing biologically important gases in vivo. The gas sensor includes an emulsoid of an aqueous dye containing buffer solution in a gas permeable cross-linked polymer.

In may situations, it is extremely important to determine the partial pressure of a gas in a fluid. One such situation is the determination of blood gas in warm blooded animals as for instance the concentration of blood gas in a human patient's blood during the performance of medical procedure on that patient.

Lubbers et al, U.S. Pat. Res. No. 31,879, describes an apparatus for making such a determination. The apparatus of Lubbers et al utilizes light of a particular frequency band width which is directed onto a sample cell (which Lubbers refers to as an optode). A biological fluid of interest is positioned in association with the cell for the determination of the partial pressure of the gas therein.

Heitzmann, U.S. Pat. No. 4,557,900, is also directed to as sensing devices. In Heitzmann, dye particles are taken up in a hydrophilic fluid and then are absorbed or adsorbed on carrier beads or particles. These beads or particles are then taken up in a matrix of a hydrophobic material. Thus for instance Heitzmann forms a solution of beta-methylum-belliferone in sodium bicarbonate and absorbs this solution into the voids of polyacrylamide particles. These particles are of the order of 35 microns in size. The particles are then incorporated into a polymerized disk of polymeric material. The disk, which may be of a size of approximately 100 microns thick by 3 mm in diameter, is associated with a fiber optic bundle in a cassette. The cassette is then utilized for sensing blood gases.

The devices of both Lubbers et al and Heitzmann incorporate very useful blood gas measurement techniques. Both Lubbers et al and Heitzmann take advantage of fluorescent or absorption properties of a dye upon interaction either directly or indirectly with the gas of interest. The interaction of the dye with the gas is then measured spectrophotometrically. This technique has many basic merits and, in fact, similar techniques are utilizes for this invention. In both Lubbers et al and Heitzmann the before mentioned optical indicator dye is used to indirectly measure carbon dioxide through an acid-base interaction of the gas and the dye.

BRIEF DESCRIPTION OF THE INVENTION

This invention eliminates the hydrophilic beads or carrier particles of the prior art and facilitates the production of new and improved gas sensors of such a size so as to be capable of being introduced directly into the body of a patient as for instance by intravenous, intraarterial or interstitial introduction. The gas sensors of the invention are stable, reproducible and are tolerant of production variable without detracting from the inherent properties of the gas sensors.

This can be advantageously accomplished in a gas sensor which comprises a aqueous first phase including a dye and a second phase. The first phase comprises an aqueous buffer solvent and a solute, the solute including the dye, the dye being soluble in the aqueous buffer solvent. The second phase comprises a cross-lined polymeric material which is gas permeable, light permeable and essentially aqueous impermeable. The first and second phases are formed in to a permanent emulsoid of suspended dispersed micro-compartments of the aqueous first phase in the cross-linked polymeric second phase wherein the micro-compartments of the aqueous first phase are essentially smaller than 5 microns.

In an illustrative embodiment of the invention, the dye is a pH sensitive dye, the aqueous buffer solvent is a physiological pH range buffer solution as for instance a bicarbonate ion based buffer solution. In this illustrative embodiment the polymeric material is a silicon material as for instance a siloxane material which is carbon dioxide permeable. More specifically the material is polydimethysiloxane. The dye in the illustrative embodiment is hydroxypyrene trisulfonic acid and the micro-compartments of the aqueous first phase are essentially smaller then 2 microns.

In an illustrative embodiment the permanent emulsoid is formed as a three dimensional structure having essentially orthogonal axes and wherein the outside dimension of the structure as measured along any of the axes is not greater than 125 microns.

In an illustrative embodiment, the aqueous first phase can further include a least one emulsification enhancement agent as for instance an emulsification enhancement agent chosen from the group consisting of water soluble dextran and polyvinylalcohol. In these illustrative embodiments, the water soluble dextran would have a molecular weight of approximately 500,000 molecular weight units. Further an osmorequlatory agent and a bacteriostatic agent can be added.

A further advantageous process of preparing a gas sensor comprises a dissolving a quantity of a dye in a quantity of aqueous buffer solution followed by vigorously mixing the buffer solution with a quantity of a polymeric precursor of a cross-lined polymeric material so as to form an emulsion of the buffer solution and the polymeric precursor. Then a quantity of a cross-linking agent is added to the emulsion. A catalyst would be added either to the polymeric precursor or with the cross-linking agent. The catalyzed emulsion is formed into a shape and the shaped catalyzed emulsion cured by aging to form a permanent emulsoid of micro-compartments of the dye containing aqueous buffer solution in the cross-linked polymeric material.

The above process can be augmented by adding a quantity of an emulsification enhancement agent to the solution of the dye in the buffer so as to form a solution of the dye and the emulsification enhancement agent in the buffer.

In an illustrative embodiment of the process, the dye is present in the aqueous phase in a consenctration of about 2 to about 50 millimolar and the buffer is present in the aqueous phase in a concentration of from about 2 to about 50 millimolar. The aqueous phase solution of the dye in the buffer is added to the polymeric precursor in a quantity of about 1 gram of the aqueous solution to about to about 4 grams of the aqueous solution per 10 grams of the polymeric precursor. The cross-linking agent is added in a quantity of about 0.5 grams of the cross-linking agent to about 2 grams of the cross-linking agent per 10 grams of he polymeric precursor and the catalyst is present in trace amounts.

If the emulsification enhancement agent is used, the emulsification enhancement agent is add to the buffer solution in a amount of about 10% to about 30% by weight of the emulsification enhancement agent per the weight of the buffer solution.

BRIEF DESCRIPTION OF THE DRAWING

This invention will be better understood when taken in conjunction with the drawing wherein.

This invention utilizes certain principles and/or concepts as are set forth in the claims appended to this specification. Those skilled in the gas sensing arts to which this invention pertains will realize that these principles and/or concepts are capable of being illustrated in a variety of embodiments which may differ from the exact embodiments utilized for illustrative purposes in this specification. For these reasons, the invention described in this specification is not to be construed as being limited to only the illustrative embodiments but is only to be construed in view of the appended claims.

DETAILED DESCRIPTION OF THE INVENTION

This invention is directed to a gas sensor which can be utilized with a fiber optical cable, i.e. a single optical fiber or a bundle of the same. The fiber optic cable is associated with appropriate optical and electronic devices for imposing an optical signal on the fiber and for reading a return optical signal from the gas sensor. A plurality of techniques for transmitting and reading appropriate optical signals can be utilized with the gas sensors of the invention. Since the optics and electronics for gas sensing do not form a apart of this invention, for brevity of this specification, these will not be reviewed in detail, references being made to the above referenced patents to Lubbers et al and Heitzmann. For these reasons the entire disclosures of U.S. Pat. No. Re. 31,879 to Lubbers et al and U.S. Pat. No. 4,557,900 to Heitzmann are herein incorporated by reference.

As with the above referenced patents to Lubbers et al and Heitzmann, dye or optical indictor is utilized for sensing a gas of interest. The dye can be one which acts with the gas of interest either by directly interacting with the gas or by indirectly acting with the gas, as for example by sensing a pH change in a medium wherein the pH change is caused by interaction of the gas of interest with that medium. Interaction of the gas of interest with the dye, either directly or indirectly, can be monitored by any suitable optical technique as for instance by either fluorescence or by absorption.

A suitable optical fiber for carrying an optical signal to and form a gas sensor typically need be no bigger than 125 microns in diameter. Certain prior known gas sensors are many fold times bigger than such a optical fibers, as for instance the 3000 micron diameter disk of Heitzmann. The gas sensor of this invention can be sized so as to be of the same dimensional realm as such a typical 125 micron optical fiber. In view of this, it is possible to mount the gas sensor of this invention directly on the optical fiber utilizing suitable mounting techniques. A so mounted, together both the gas sensor and its combination supporting and signal carrying optical fiber can be inserted directed into a system of interest as for instance directly into a patient's cardiovascular system, intramuscularly or into other body organs such as the lungs and the like.

In constructing a gas or sensor of this invention, we form a solution of a suitable indicator dye in an aqueous buffer. The aqueous phase is then emulsified with a liquid precursor of a polymeric material. During the emulsification step, the aqueous phase is broken up in to very small droplet sizes. The polymeric material is chosen such that the aqueous phase is not soluble in either the precursor materials for the polymeric material or the polymerized polymeric material. Thus the aqueous phase always retains its integrity.

By emulsifying the aqueous phase into the polymeric precursor materials, very small discrete "micro-compartments" or cells of the aqueous phase can be formed in the polymeric phase. Upon polymerization, these micro-compartments are "frozen" or fixed in dispersed positions which are essentially uniformly scattered through out the polymeric material. An emulsoid of the aqueous phase is thus formed in the polymeric phase.

Since the aqueous phase is very evenly distributed within the polymeric phase, when it is fixed in position in the emulsoid, its concentration is very evenly distributed throughout the emulsoid. Because the concentration of the aqueous phase is uniform through the emulsoid, the sensing characterics of the gas sensor of the invention are also very uniform.

Contrary to other gas sensors, by using very small emulsion sized particles, the surface area of the individual micro-compartments and thus the totality of the micro-compartments of the aqueous phase is very large. Gas exchange between the polymeric phase and the aqueous phase is across the interface between the surface of the aqueous phase and the polymeric phase. Because the surface area of the aqueous phase which is in contact with the surface area of the polymeric phase is very large, for the gas sensors of this invention, gas exchange to the sensing aqueous phase is fast and is uniformly sensitive to the gas concentration within the polymeric phase.

By emulsifying the aqueous phase into the polymeric phase, there is no necessity for a further supporting phase as in other prior art devices. Greater miniaturization is thus possible by elimination of the support phase particles which are of a size domain much greater than the size domain of the individual aqueous phase micro-compartments of this invention. With support phase particles eliminated, each of the droplets is in contact over substantially its full surface area with the polymeric phase and is solely supported by the polymeric phase.

At a minimum, the aqueous phase must contain an indictor of the gas of interest for which the sensor is being used. Other materials can be incorporated into the aqueous phase micro-compartments. The aqueous phase must however serve as a solvent for these other materials, that is they must all be in the solute of the aqueous phase. Depending on the gas of interest, these other materials would be chosen to contribute to the operating characteristics of the gas sensor. As for instance, these additional materials can be added to promote the emulsification of the aqueous phase into the polymeric phase. Further they can be added to lower the vapor pressure of the aqueous phase in the polymeric phase so as to retard the evaporation of the aqueous phase during formation of the gas sensor of interest.

Aside from materials which contribute to the physical formation of the emulsoid of the aqueous phase in the polymeric phase, further additives can be added to the aqueous phase for enhancement of the storage and/or operating characteristics of the gas sensor as for instance bacteriostataic and/or osmoregulatory agents. These would also be chosen to be part of the solute of the aqueous first phase.

The polymeric phase is chosen as a carrier for the aqueous phase and to maintain the individual microcompartments of the aqueous phase in their dispersed form. The polymeric phase musts be permeable to the gas of interest. It must also be permeable to the wavelength or wavelengths of light utilized in the measurement of the gas of interest. Further since it is necessary to maintain the aqueous phase isolated from the carrier fluid of the gas of interest, the polymeric phase must be impermeable to liquid water. In order to isolate the indicator and/or any other ingredients in the aqueous phase, the polymeric phase must also be impermeable to ionic species. As for instance if the aqueous phase contains a buffer, it is important to maintain the ionic concentration of the buffer ions constant and not to dilute out or to increase the concentration of these desired buffer ions.

Fillers can be added to the polymeric phase. However it is important that if such fillers are added, they contribute only to desired or enhanced properties of the polymeric phase and do not interfere with or detract from the aqueous phase or the emulsification of the aqueous phase into the polymeric phase. Any such filler in the polymeric phase would not be of a size or nature to serve as carrier particles for the aqueous phase. They would be added to enhance the structural characteristics of the polymeric phase. Such enhancements might be made to reinforce the polymeric phase or to stabilize the polymeric phase. Depending of the polymeric phase material, catalyst molecules or particles might also remain in the polymeric phase after completion of the polymerization, as for instance metallic catalyst particles.

A particular gas of interest for the gas sensor of this invention is carbon dioxide. For sensing carbon dioxide a pH sensitive dye would be solubilized in the aqueous phase. Gas exchange through the polymeric phase and into the aqueous phase solubilizes the carbon dioxide gas in the aqueous phase as carbonic acid which interacts with the buffer ions. The dye chosen is one which is responsive to the concentrations of the ionic species of the carbonic acid in the aqueous phase, i.e. an acid-base responsive dye.

Preferred for use in sensing carbon dioxide is a bicarbonate ion based buffer aqueous phase. Such a buffer can be chosen so as to have a buffer range compatible with the response range of the dye. Such a range might, for instance, mimick the physiological pH range of blood. Suitable for the preparation of such a bicarbonate ion buffer would be sodium bicarbonate, sodium carbonate and sodium hydroxide or other suitable buffer agents. For measuring blood carbon dioxide with hydroxypyrene trisulfonic acid, a pH range of pH 7.0 to pH 8.0 is the most desirable.

In choosing a dye for measuring carbon dioxide in blood, consideration is given to matching the pKa of the dye to the pH range of the buffer induced by physical $CO_2$ levels. In constructing a gas sensor of this invention for use in sensing carbon dioxide gas in blood, we have found that hydroxypyrene 3,6,8-trisulfonic acid has characterics which are superior to beta-methyumbelliferone. although beta-methylumbelliferone can also be used. Hydroxypyrene 3,6,8-trisulfonic acid, hereinafter referred to as HPTS, which is a known fluorescence dye for carbon dioxide, has a larger "Strokes shift" than does the umbelliferone compound. For use in fluorescences spectroscopy, this separates the excitation light from the emission light which improves the measurement of the emission light for improved gas sensor performance. The hydroxypyrene trisulfonic acid can be used as a free acid or as one of its salts as for instance an alkali or alkali earth salt.

In addition to the above mentioned HPTS and umbelliferone compound, other fluorescent dyes such as fluorescein could be used. Also absorption dyes such as chlorophenol red, bromo cresol purple, nitrophenol, bromo thymol blue, pinachorome and phenol red could be used.

Because of their high gas permeability and water impermeability, silicone polymers are preferred. For use in forming a carbon dioxide gas sensor, polydimethysiloxane is preferred. A particular useful commercial polydimethysiloxane is sold by Petrarch Systems, Inc. under the trademark PE1055. It is used in conjunction with a cross-linking agent Petrarch PE1055 cross-linker or Petrarch PE123 cross-liner. The PE1055 has a platinum catalyst incorporated into the polymeric precursor which is retained in the polymerized polymer. Its presence in the finished gas sensor does not detract from the characterics of the gas sensor. With other polymers, volatile or short lived catalysts such as a free radical catalyst could be used.

The silicon polymeric phase can be prepared via two polymerization reactions. Aside from the above described addition type polymerization, the silicon polymeric phase can also be prepared via condensation polymerization reactions using silanol terminated silicones cross-linked with alkoxyl silanes using catyalsts such as tin derivatives.

The above noted PE1055 siloxane precursor also contains a fumed silica filler. This filler enhances the stability of the aqueous dispersion and the tear strength of the final polymeric product.

During manufacturing of the carbon dioxide sensor of the invention, the above noted HPTS is taken up in an appropriate buffer solution. An appropriate bacteriostatic agent such as thimerosal is added as is sodium chloride as an osmoregulatory agent.

Certain properties of the emulsion between the aqueous phase and the polymeric precursor can be enhanced by adding additional agents herein identified by the terminology "emulsification enhancement agents". These emulsification enhancement agents enhance certain manufacturin properties such as shelf life of the gas sensor intermediates by stabilizing the emulsion and retarding dehydration of the aqueous phase. In general these emulsification enhancement agents are hydrophilic macro molecules.

By retarding the dehydration of the aqueous phase and break down of the emulsion of the aqueous phase and the polymeric precursor, it is not mandatory to immediately polymerize the aqueous phase-polymeric precursor emulsion into the emulsoid gas sensor of the invention. With the addition of the emulsification enhancement agents, the emulsion of the aqueous phase and polymeric precursor is stable and can set aside for formation into the emulsoid gas sensor of the invention at a later time. This reduces adhering to a tight manufacturing schedule and reduces or prevents the generation of manufacturing "scrap materials" which are economically wasteful.

Suitable for use as the above mentioned hydrophilic macro molecules used as the emulsification enhancement agents would be agents such as water soluble dextran. Also considered might be polyvinylalcohol. For use in this invention, water soluble dextran as opposed to cross-linked dextran would be used to insure its water solubility. One such water soluble dextran is dextran of a molecular weight of about 500,000. In any event, if added the emulsification enhancement agent or any other agents such as the before mentioned bacteriostatic or osmoregulatory agents would be water soluble and would form part of the solute of the aqueous buffer phase. Since in the finished gas sensor of this invention, these solute agents always remain in solution even in the finished gas sensor, they do not detract from the above noted properties of the gas sensor of this invention.

Generally the concentration of the dye in the aqueous phase would be from about 2 millimolar to about 50 millimolar with about a 10 millimolar solution being typically used. Generally the concentration of the buffer in the aqueous phase would be from about 2 millimolar to about 50 millimolar with about a 20 millimolar solution typically being used. If used, the emulsification enhancement agent would be present at from about 10% to abut 30% by weight per weight of the water of the aqueous phase. Typically about a 25% by weight of the emulsification enhancement agent is used. From about 1 grams to about 4 grams of the aqueous solution would be added to about 10 grams of the polymeric precursor. Typically about 2 grams of the aqueous phase per 10 grams of the polymeric precursor is used. The cross-linking agent would be added from about 5% to about 20% by weight of the polymeric precursor with approximately 10% by weight with respect to the weight of the polymeric precursor typically being used.

In an illustrative embodiment of the invention the dye is present in a quantity of about 0.01 grams per 2 mls. of said buffer solution, the dye in the buffer solution is added to the polymeric precursor in a quantity of about 2 mls. of the dye in the buffer solution to a bout 10 grams of the polymeric precursor. The cross-lining agent is added in a quantity of about 1 gram of the cross-linking agent per 10 grams of the polymeric precursor and the catalyst is present in trace amounts.

When the mixture of the aqueous phase and the polymeric precursor is emulsified, a suitable homogenizer such as a Virtis 23 homogenizer is used. The emulsification enhancement agent contributes to stability of the emulsion such that it has an increased shelf life. When it is desired to form the gas sensor of the invention, the cross-linker is added, as is the catalyst if it is not already present in the polymeric precursor. These are gently stirred into the emulsion and the resulting mixture then shaped and cured by aging. A very simple gas sensor can be formed by simply depositing a drop of the mixture of the emulsion and the cross-linking agent on to the end of a fiber optic fiber and allowing it to cure into an emulsoid directly on the end of the fiber.

Following emulsification, the aqueous phase is present in the polymeric precursor in micro-compartments which are generally essentially smaller than 5 microns. Typically a production gas sensor of the invention will have micro compartments of the aqueous phase in the polymeric phase wherein the majority of the population of the compartments will be on the order of 2 microns. It is of course realized that the particles will actually be in a statistical range of particle sizes, some slightly larger than the above noted sizes, some slight smaller, depending on the emulsification procedure and apparatus.

Figures 1, 2:
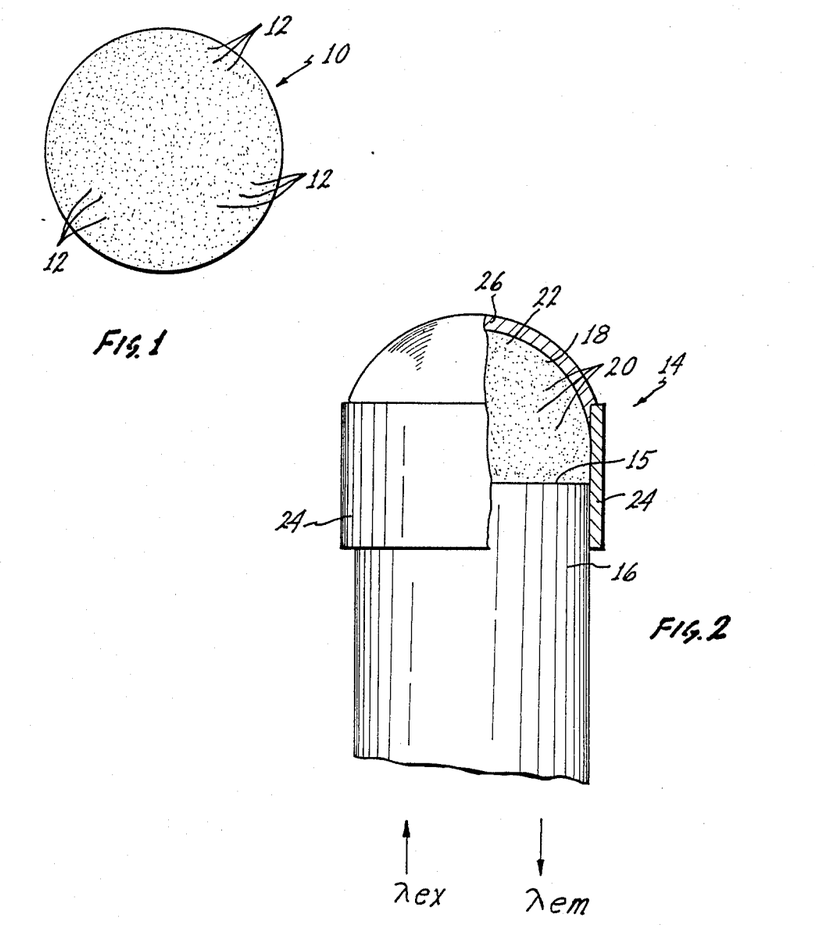
FIG. 1 is a elevational view in section of a droplet of material utilized in the preparation of a gas sensor of the invention.
FIG. 2 is an elevational view in partial section of a gas sensor of the invention.

Seen in FIG. 1 is a drop 10 of the emulsion of the aqueous phase in the polymeric precursor. As is evident the micro-compartments 12 are dispersed in a uniform manner through the drop 10 of the emulsion.

For formation of a very simple gas sensor 14 of this invention, in FIG. 2, drop of the above mixture is placed on the distal end 15 of an optical fiber 16. As the mixture of the cross-linking agent and the polymeric precursor having the aqueous phase as a emulsion therein, ages, it cures into an emulsoid 18 of the micro-compartments 20 of the aqueous phase in the polymeric material or carrier body 22. If desired, the emulsoid 18 can be retained on the end of the fiber 16 using a suitable sleeve 24. The sleeve 24 can be constructed from a suitable material such as Teflon or the like. Further to avoid light intensity changes caused by factors other than the changes in patial pressure of the gas sensed, an overcoat 26 can be added as a layer over the exposed positions of the emulsoid 18. For use with a fluorescent dye, the overcoat 26 is chosen to be opaque to the excitation light wavelength $\lambda_{ex}$ and to the emission light wavelength $\lambda_{em}$ both of which are transmitted along the same single optical fiber 16. A suitable material for the overcoat 26 would be cellulose impregnated with carbon black.

As is evident in FIG. 2, the size of the gas sensor 14 is dictated only by the optical fiber size. The gas sensor 14 thus formed is of a sufficiently small size so as to be introducible directed into the cardiovascular system of a patient for direct real time measurement of the partial pressure of a blood gas such a s carbon dioxide. If the fiber optic fiber 16 of FIG. 2 is typically about 125 micron in diameter, it is evident that the emulsoid 18 is approximately equal to or less than this size in each of it orthogonally oriented width, height and depth dimensions. Other constructions of gas sensors are also possible utilizing the emulsoid of this invention. It of course being realized that smaller sensors could be constructed by utilizing a smaller diameter fiber optic cable.

By using the above noted gas sensor construction in conjunction with HPTS as a carbon dioxide sensitive dye, determination time of the gas of interest is made in a time period of approximately one minute. This gas sensor can be autoclaved to sterilize it without detracting from or degrading it performance and during its use it is essentially temperature stable.

The following embodiment is offered as an illustration for the preparation of a gas sensor of the invention.

0.1048 grams of HPTS, 0.0106 grams of sodium bicarbonate, 0.1284 grams of sodium chloride 6.666 grams of 500,000 mol. wt. dextran and 0.02 grams of thimerasol were dissolved in 20 grams of water. 2 mls of the above aqueous solution was mixed with 10 grams of Petarach PE1055, which contained a trace amount of a platinum catalyst, in a Virtis 23 homogenizer for 30 seconds at moderate speed then for 3 minutes at high speed with a cooling time inbetween of 30 to 45 seconds to form an emulsion. 1.0 grams of Petarach PE1055 cross-linker was added and stirred into the other ingredients. A drop of the final emulsion was then placed on the end of a 125 micron diameter fiber optic cable to form a carbon dioxide as sensor. The aqueous phase micro compartments in this sensor were on the order of approximately 2 microns in diameter. The final sensor itself, has dimension approximately equal to that of the fiber optic cable. In each of the three X, Y, and Z orthogonal axes, the sensor was less then 125 microns in size.

We claim:

1. A gas sensing composition which comprises:
   suspended dispersed microcompartments of an aqueous first phase in a cross-linked polymeric second phase wherein said aqueous first phase is present in micro-compartments smaller that 5 microns, said first phase comprising an aqueous buffer solvent and a solute, said solute including a dye soluble in said solvent, and said second cross-linked polymeric phase comprising a gas permeable, light permeable, ion impermeable and substantially aqueous impermeable polymeric material.

2. A gas sensing composition of claim 1 wherein:
   said second phase comprises a carbon dioxide permeable polymeric material.

3. A gas sensing composition of claim 1 wherein:
   said micro-compartments of said aqueous first phase are of a size essentially less than about 2 microns.

4. A gas sensing composition of claim 1 which is formed as a three dimensional structure having essentially orthogonal axes and wherein the outside dimension of said structure as measured along any of said axes is not greater that 125 microns.

5. A gas sensing composition of claim 1 wherein:
   said solute further includes a bacteriostatic agent and an osmoregulatory agent.

6. A gas sensing composition of claim 1 wherein:
   said dye is a pH sensitive dye.

7. A gas sensing composition of claim 6 wherein:
   said dye is hydroxypyrene trisulfonic acid or a salt thereof.

8. A gas sensing composition of claim 1 wherein:
   said aqueous buffer solvent has a pH buffer range from about 7.0 to about 8.0.

9. A gas sensing composition of claim 8 wherein:
   said buffer solution is a bicarbonate ion based buffer solution.

10. A gas sensing composition of claim 1 wherein:
    said material is a silicone material.

11. A gas sensing composition of claim 10 wherein:
    said material is polydimethysiloxane.

12. A gas sensing composition of claim 1 wherein:
    said aqueous first phase further includes a least one emulsification enhancement agent.

13. A gas sensing composition of claim 12 wherein:
    said emulsification enhancement agent comprises a hydrophilic macro molecule.

14. A gas sensing composition of claim 13 wherein:
    said hydrophilic macro molecule is chosen from the group consisting of water soluble dextran and polyvinyl-alcohol.

15. A gas sensing composition of claim 14 wherein:
    said hydrophitic macro molecule is dextran which has a molecular weight of approximately 500,000 molecular weight units.

16. A carbon dioxide gas sensing composition which comprises:
    a quantity of a first phase dispersed in a quantity of a second phase as a plurality of isolates smaller than 5 microns, said first phase comprising a quantity of hydroxypyrene trisulfonic acid in an aqueous buffer solution and said second phase comprises a quantity of a gas permeable, light permeable ion impermeable and substantially aqueous impermeable polymeric material.

17. The gas sensor of claim 16 wherein:
    said aqueous buffer solution comprises a bicarbonate ion based buffer solution; and
    said polymeric material comprises a siloxane polymer.

18. A gas sensor which comprises:
    an aqueous phase having an aqueous soluble optical indicator dye dissolved therein;
    a gas permeable carrier body which is essentially aqueous impermeable and ion impermeable and is capable of transmitting light at least at selected wavelengths;
    a plurality of droplets of said aqueous phase dispersed in said carrier body, said droplets being supported by said carrier body;
    an optical fiber having an optical face; and
    said carrier body with said aqueous phase dispersed therein being located in association with said optical face of said optical fiber.

19. A gas sensor of claim 18 further including:
    said carrier body with said aqueous phase dispersed therein being located directly on said optical face; and
    an overcoat located on at least a portion of said carrier body which is not located directly on said optical face, said overcoat being substantially opaque to at least said selected wavelengths of light characteristic of said dye.

20. A gas sensor of claim 19 wherein:
    said optical indicator is a fluorescent dye and said selected wavelengths include the excitation and emission wavelengths of said fluoroscent dye.

21. A gas sensing composition comprising:
    a gas permeable, light permeable ion impermeable and substantially aqueous impermeable matrix consisting essentially of a single polymeric material, said matrix having a plurality of micro-compartments dispersed therein; and
    an aqueous phase in said micro-compartments and substantially filling said micro-compartments, said aqueous phase comprising an aqueous buffer solvent and a solute, said solute including a dye soluble in said solvent.

22. A gas sensor comprising:
    a gas sensing composition which comprises suspended dispersed micro-compartments of an aqueous first phase in a cross-linked polymeric second phase wherein said aqueous first phase is present in micro-compartments smaller than 5 microns, said first phase comprising an aqueous buffer solvent and a solute, said solute including a dye soluble in said solvent, and said second cross-linked polymeric phase comprising a gas permeable, light permeable, ion impermeable and substantially aqueous impermeable polymeric material; and
    optical fiber means on which said gas sensing composition is located for transmitting signals from said gas sensing composition.

23. A gas sensor of claim 22 wherein:
    said micro-compartments of said aqueous first phase are of a size essentially less than about 2 microns.

24. A gas sensor of claim 2 wherein:
    said gas sensing composition is formed as a three dimensional structure having essentially orthogonal axes and the outside dimension of said structure as measured along any of said axes is not greater than 125 microns.

25. A carbon dioxide gas sensor comprising:

a carbon dioxide gas sensing composition which comprises a quantity of a first phase dispersed in a quantity of second phase as a plurality of isolates smaller than 5 microns, said first phase comprising a quantity of hydroxypyrene trisulfonic acid in an aqueous buffer solution and said second phase comprises a quantity of gas permeable, light permeable, ion impermeable and substantially aqueous impermeable polymeric material and;

optical fiber means on which said carbon dioxide gas sensing composition is located for transmitting signals from said carbon dioxide gas sensing composition.

26. A gas sensor comprising:

a gas permeable, light permeable, substantially aqueous impermeable and ion impermeable matrix consisting essentially of a single polymeric material, said matrix having a plurality of micro-compartments dispersed therein; and an aqueous phase in said micro-compartments and substantially filling said micro-compartments, said aqueous phase comprising an aqueous buffer solvent and a solute, said solute including a dye soluble in said solvent; and optical fiber means on which said matrix is located for transmitting signals from said dye.

* * * * *

UNITED STATES PATENT AND TRADEMARK OFFICE
CERTIFICATE OF CORRECTION

PATENT NO. : 4,824,789

DATED : Apr. 25, 1989

INVENTOR(S) : Yafuso et al

It is certified that error appears in the above-identified patent and that said Letters Patent is hereby corrected as shown below:

Column 1, line 6 change "sue" to -- use --.

Column 1, line 10 change "may" to -- many --.

Column 1, line 67 change "cross-lined" to -- cross-linked --.

Column 2, line 34 after "comprises" delete "a".

Column 2, line 36 change "cross-lined" to -- cross-linked --.

Column 2, line 54 change "conscentration" to -- concentration --.

Column 2, line 60 delete the second occurrence of "to about".

Column 2, line 66 change "add" to -- added --.

Column 3, line 65 change "A so" to -- As so --.

Column 4, line 3 after "gas" delete "or".

Column 5, line 10 change "musts" to -- must --.

Column 5, line 68 change "although" to -- Although --.

Column 6, line 25 change "cross-liner" to -- cross-linker --.

Column 6, line 53 change "manufacturin" to -- manufacturing --.

Column 7, line 43 change "a bout" to -- about --.

Column 7, line 44 change "cross-lining" to -- cross-linking --.

UNITED STATES PATENT AND TRADEMARK OFFICE
CERTIFICATE OF CORRECTION

PATENT NO. : 4,824,789

DATED : Apr. 25, 1989

INVENTOR(S) : Yafuso et al

It is certified that error appears in the above-identified patent and that said Letters Patent is hereby corrected as shown below:

Column 8, line 3 change "slight" to -- slightly --.

Column 8, line 14 change "a emulsion" to -- an emulsion --.

Column 8, line 22 change "patial" to -- partial --.

Column 8, line 37 change "such a s" to -- such as --.

Column 8, line 39 change "each of it" to -- each of its --.

Column 8, line 50 change "degrading it" to -- degrading its --.

Column 8, line 67 change "as sensor" to -- gas sensor --.

Column 9, line 10 change "smaller that" to -- smaller than --.

Column 9, line 27 change "greater that" to -- greater than --.

Signed and Sealed this

Thirtieth Day of April, 1991

Attest:

HARRY F. MANBECK, JR.

Attesting Officer

Commissioner of Patents and Trademarks

REEXAMINATION CERTIFICATE (2969th)
United States Patent [19]
Yafuso et al.

[11] B1 4,824,789
[45] Certificate Issued Aug. 13, 1996

[54] GAS SENSOR

[75] Inventors: Masao Yafuso, El Toro; John K. Suzuki, San Juan Capistrano, both of Calif.

[73] Assignee: Minnesota Mining and Manufacturing Company, Saint Paul, Minn.

Reexamination Request:
No. 90/003,660, Dec. 13, 1994

Reexamination Certificate for:
Patent No.: 4,824,789
Issued: Apr. 25, 1989
Appl. No.: 917,912
Filed: Oct. 10, 1986

Certificate of Correction issued Apr. 13, 1991.

[51] Int. Cl.$^6$ .............................. G01N 33/49; G02B 6/02
[52] U.S. Cl. .................. 436/68; 436/133; 436/172; 128/634; 250/227; 356/39; 422/58; 422/83
[58] Field of Search .................. 436/58, 68, 172, 436/133; 422/58, 83; 128/634; 356/39; 250/227

[56] References Cited

U.S. PATENT DOCUMENTS

| | | | |
|---|---|---|---|
| 4,577,109 | 3/1986 | Hirschfeld | 250/461.1 |
| 4,824,789 | 4/1989 | Yafuso et al. | 436/68 |

FOREIGN PATENT DOCUMENTS

0105870B1  4/1984  European Pat. Off. .

*Primary Examiner*—Lyle Alfandary-Alexander

[57] ABSTRACT

A gas sensor has a first aqueous phase. The aqueous phase is composed of a soluble dye in a buffer. One or more additional agent can be further added to the aqueous phase as for instance an emulisification enhancement agent. The aqueous phase is homogenized into a polymeric precursor forming a emulsion of the aqueous phase in the polymeric precursor. A catalyst and a cross-linking agent are added and the polymeric precursor material allowed to polymerize to form an emulsoid of micro-compartments of the aqueous phase in a polymeric second phase. The micro-compartments of the aqueous phase are dispersed through and permanently suspended in the polymeric second phase.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 12 is cancelled.

Claims 1, 13, 15–18, 21–22 and 24–26 are determined to be patentable as amended.

Claims 2–11, 14, 19–20 and 23, dependent on an amended claim, are determined to be patentable.

New claims 27–31 are added and determined to be patentable.

1. A gas sensing composition which comprises:
suspended dispersed microcompartments of an aqueous first phase in a cross-linked polymeric second phase wherein said aqueous first phase is present in micro-compartments smaller than 5 microns, said first phase comprising an aqueous buffer solvent, [and] a solute, *and at least one emulsification enhancement agent,* said solute including a dye soluble in said solvent, and said second cross-linked polymeric phase comprising a gas permeable, light permeable, ion impermeable and substantially aqueous impermeable polymeric material.

13. A gas sensing composition of claim [12] *1* wherein:
said emulsification enhancement agent comprises a hydrophilic macro molecule.

15. A gas sensing composition of claim 14 wherein:
said [hydrophitic] *hydrophilic* macro molecule is dextran which has a molecular weight of approximately 500,000 molecular weight units.

16. A carbon dioxide gas sensing composition which comprises:
a quantity of a first phase dispersed in a quantity of a second phase as a plurality of isolates smaller than 5 microns, said first phase comprising a quantity of hydroxypyrene trisulfonic acid *and water soluble dextran* in an aqueous buffer solution, and said second phase comprises a quantity of a gas permeable, light permeable, ion impermeable and substantially aqueous impermeable polymeric material.

17. The gas [sensor] *sensing composition* of claim 16 wherein:
said aqueous buffer solution comprises a bicarbonate ion based buffer solution; and
said polymeric material comprises a siloxane polymer.

18. A gas sensor which comprises:
an aqueous phase having an aqueous soluble optical indicator dye *and an aqueous soluble emulsification agent* dissolved therein;
a gas permeable carrier body which is essentially aqueous impermeable and ion impermeable and is capable of transmitting light at least at selected wavelengths;
a plurality of droplets of said aqueous phase dispersed in said carrier body *as micro-compartments essentially smaller than 5 microns*, said droplets being supported by said carrier body;
an optical fiber having an optical face; and
said carrier body with said aqueous phase dispersed therein being located in association with said optical face of said optical fiber.

21. A gas sensing composition comprising:
a gas permeable, light permeable, ion impermeable and substantially aqueous impermeable matrix consisting essentially of a single polymeric material, said matrix having a plurality of micro-compartments dispersed therein, *each micro-compartment being essentially smaller than 5 microns*; and
an aqueous phase in said micro-compartments and substantially filling said micro-compartments, said aqueous phase comprising an aqueous buffer solvent, [and] a solute, *and at least one emulsification enhancement agent,* said solute including a dye soluble in said solvent.

22. A gas sensor comprising:
a gas sensing composition which comprises suspended dispersed micro-compartments of an aqueous first phase in a cross-linked polymeric second phase wherein said aqueous first phase is present in micro-compartments smaller than 5 microns, said first phase comprising an aqueous buffer solvent, [and] a solute, *and at least one emulsification enhancement agent,* said solute including a dye soluble in said solvent, and said second cross-linked polymeric phase comprising a gas permeable, light permeable, ion impermeable and substantially aqueous impermeable polymeric material; and
optical fiber means on which said gas sensing composition is located for transmitting signals from said gas sensing composition.

24. A gas sensor of claim [2] *22* wherein:
said gas sensing composition is formed as a three dimensional structure having essentially orthogonal axes and the outside dimension of said structure as measured along any of said axes is not greater that 125 microns.

25. A carbon dioxide gas sensor comprising:
a carbon dioxide gas sensing composition which comprises a quantity of a first phase dispersed in a quantity of second phase as a plurality of isolates smaller than 5 microns, said first phase comprising a quantity of hydroxypyrene trisulfonic acid *and water soluble dextran* in an aqueous buffer solution, and said second phase comprises a quantity of gas permeable, light permeable, ion impermeable and substantially aqueous impermeable polymeric material; *and* [;]
optical fiber means on which said carbon dioxide gas sensing composition is located for transmitting signals from said carbon dioxide gas sensing composition.

26. A gas sensor comprising:
a gas permeable, light permeable, substantially aqueous impermeable and ion impermeable matrix consisting essentially of a single polymeric material, said matrix having a plurality of micro-compartments dispersed therein, *each micro-compartment being essentially smaller than 5 microns*; and
an aqueous phase in said micro-compartments and substantially filling said micro-compartments, said aqueous phase comprising an aqueous buffer solvent, [and]

a solute, *and at least one emulsification enhancement agent,* said solute including a dye soluble in said solvent; and optical fiber means on which said matrix is located for transmitting signals from said dye.

27. A gas sensing composition of claim 1 wherein:

*said cross-linked polymeric second phase includes a filler.*

28. The gas sensing composition of claim 17 wherein:

*said siloxane polymer contains a fumed silica filler.*

29. A gas sensing composition of claim 21 wherein:

*said polymeric material includes a filler.*

30. *A carbon dioxide gas sensing composition which comprises:*

*a quantity of a first phase dispersed in a quantity of a second phase as a plurality of isolates smaller than 2 microns, said first phase comprising a quantity of hydroxypyrene trisulfonic acid, thimerosal, and water soluble dextran having a molecular weight of approximately 500,000 molecular weight units in a bicarbonate ion based buffer solution having a pH buffer range from about 7.0 to about 8.0, and said second phase comprises a siloxane polymer containing a fumed silica filler.*

31. *A carbon dioxide gas sensor comprising:*

*a carbon dioxide gas sensing composition which comprises a quantity of a first phase dispersed in a quantity of a second phase as a plurality of isolates smaller than 2 microns, said first phase comprising a quantity of hydroxypyrene trisulfonic acid, thimerosal, and water soluble dextran having a molecular weight of approximately 500,000 molecular weight units in a bicarbonate ion based buffer solution having a pH buffer range from about 7.0 to about 8.0, and said second phase comprises a siloxane polymer containing a fumed silica filler;*

*optical fiber means on which said carbon dioxide gas sensing composition is located for transmitting signals from said carbon dioxide gas sensing composition; and*

*an overcoat located on at least a portion of said carbon dioxide gas sensing composition, said overcoat being substantially opaque to selected wave lengths of light characteristic of the hydroxypyrene trisulfonic acid.*

* * * * *